(12) United States Patent
Cain et al.

(10) Patent No.: US 12,035,948 B2
(45) Date of Patent: *Jul. 16, 2024

(54) CLIP-ON REDUCER

(71) Applicant: Spinal Elements, Inc., Carlsbad, CA (US)

(72) Inventors: David Brett Cain, Marietta, GA (US); Joshua David Gunn, Woodstock, GA (US)

(73) Assignee: Spinal Elements, Inc., Carlsbad, CA (US)

( * ) Notice: Subject to any disclaimer, the term of this patent is extended or adjusted under 35 U.S.C. 154(b) by 359 days.

This patent is subject to a terminal disclaimer.

(21) Appl. No.: 16/916,587

(22) Filed: Jun. 30, 2020

(65) Prior Publication Data

US 2020/0323567 A1    Oct. 15, 2020

Related U.S. Application Data

(63) Continuation of application No. 16/108,751, filed on Aug. 22, 2018, now Pat. No. 10,729,477, which is a continuation of application No. 15/229,917, filed on Aug. 5, 2016, now Pat. No. 10,080,594.

(51) Int. Cl.
| | |
|---|---|
| *A61B 17/70* | (2006.01) |
| *A61B 17/88* | (2006.01) |
| *A61B 17/56* | (2006.01) |
| *A61B 17/68* | (2006.01) |

(52) U.S. Cl.
CPC ...... *A61B 17/7086* (2013.01); *A61B 17/7091* (2013.01); *A61B 2017/567* (2013.01); *A61B 2017/681* (2013.01); *A61B 17/8875* (2013.01)

(58) Field of Classification Search
None
See application file for complete search history.

(56) References Cited

U.S. PATENT DOCUMENTS

| | | |
|---|---|---|
| 5,720,751 A | 2/1998 | Jackson |
| 7,278,995 B2 | 10/2007 | Nichols et al. |
| 7,470,279 B2 | 12/2008 | Jackson |
| 7,575,581 B2 | 8/2009 | Lovell |
| 7,608,081 B2 | 10/2009 | Abdelgany |
| 7,621,918 B2 | 11/2009 | Jackson |
| 7,824,411 B2 | 11/2010 | Varieur et al. |
| 7,824,413 B2 | 11/2010 | Varieur et al. |
| 7,842,044 B2 | 11/2010 | Runco et al. |

(Continued)

*Primary Examiner* — Tessa M Matthews

(57) ABSTRACT

A clip-on reducer tool assembly for seating a spinal fixation rod in a rod receiving implant, the tool assembly has an outer sleeve. The outer sleeve has a proximal end with a cylindrical portion having a threaded opening, a first leg extension extending therefrom to a distal end, and a second leg extension joined to the first leg extension at an intermediate location between the distal end and proximal end. The second leg extension extends from the distal end toward the proximal end to a lever end spaced from the cylindrical portion. The leg extensions at the distal end have grasping members to engage an outer surface of a rod receiving implant and a fulcrum proximally located near the intermediate location configured to enlarge the space between the leg extension at the distal end as the lever end is depressed inwardly relative to a longitudinal axis of the outer sleeve.

10 Claims, 23 Drawing Sheets

(56) References Cited

U.S. PATENT DOCUMENTS

| | | | |
|---|---|---|---|
| 7,918,857 B2 | 4/2011 | Dziedzic et al. | |
| 7,918,858 B2 | 4/2011 | Stad et al. | |
| 7,951,168 B2 | 5/2011 | Chao et al. | |
| 8,096,996 B2 | 1/2012 | Gutierrez et al. | |
| 8,246,623 B2 | 8/2012 | Peultier et al. | |
| 8,439,922 B1 | 5/2013 | Arnold et al. | |
| 8,500,750 B2 | 8/2013 | Varieur et al. | |
| 8,535,318 B2 | 9/2013 | Peterson et al. | |
| 8,617,218 B2 | 12/2013 | Justis et al. | |
| 8,641,719 B2 | 2/2014 | Gephart et al. | |
| 8,647,347 B2 | 2/2014 | Runco et al. | |
| 8,828,007 B2 | 9/2014 | Stad et al. | |
| 8,894,662 B2 | 11/2014 | Varieur et al. | |
| 9,050,139 B2* | 6/2015 | Jackson | A61B 17/7037 |
| 9,486,256 B1* | 11/2016 | Lish | A61B 17/7086 |
| 2003/0225408 A1 | 12/2003 | Nichols et al. | |
| 2006/0079909 A1* | 4/2006 | Runco | A61B 17/7086 |
| | | | 606/99 |
| 2006/0089651 A1 | 4/2006 | Trudeau et al. | |
| 2007/0021835 A1 | 1/2007 | Edidin | |
| 2007/0260261 A1 | 11/2007 | Runco et al. | |
| 2008/0228233 A1 | 9/2008 | Hoffman et al. | |
| 2009/0030419 A1 | 1/2009 | Runco et al. | |
| 2010/0036443 A1 | 2/2010 | Hutton et al. | |
| 2012/0253402 A1 | 10/2012 | McLean | |
| 2014/0277137 A1 | 9/2014 | Stad et al. | |
| 2014/0277166 A1* | 9/2014 | Brinkman | A61B 17/7086 |
| | | | 606/279 |
| 2018/0036044 A1 | 2/2018 | Cain et al. | |

* cited by examiner

CLIP-ON REDUCER

RELATED APPLICATIONS

This application is a continuation of U.S. patent application Ser. No. 16/108,751, filed Aug. 22, 2018, which is a continuation of U.S. patent application Ser. No. 15/229,917, now U.S. Pat. No. 10,080,594, filed Aug. 5, 2016, the disclosure of each incorporated by reference herein in its entirety.

TECHNICAL FIELD

The present invention relates to a tool assembly for seating a fixation rod into a spinal fixation rod receiving implant and securing the seated fixation rod as part of a vertebral corrective surgery.

BACKGROUND OF THE INVENTION

Spinal surgeons are required to implant a variety of rods, screws and plates into the bony skeletal structure of the spine to correct a variety of misalignments and repair damage that exist between the vertebral bodies. A particularly useful procedure involves the placement of rod receiving spinal implants with pedicle screws into the vertebrae. These rod receiving implants commonly have a slotted "U" shaped body with a pedicle screw extending from the base of the slotted body. When the surgeon implants these devices in the bones along the portion of the spine to be corrected, he must then connect two or more of these implants using fixation rods. The fixation rods are typically solid round cylindrical metal devices that can be straight or curved. The rods must be driven inwardly to be seated to fit between the "U" shaped slotted body. Once in a seated position, the rod can be fixed rigidly into the rod receiving implant by tightening a set screw into the threaded legs of the slotted body clamping the fixation rod securely to the slotted body.

One difficulty for the surgeon is aligning the fixation rods with the slotted rod receiving implants and moving the rod inwardly toward the slot. This is particularly difficult when the implants need to be positioned to correct a preexisting misalignment. This aspect of positioning the rod is called reduction or reducing and a variety of elongated tools have been developed to facilitate the proper placement of fixation rods.

The present invention, as described hereinafter, is an improved tool assembly that can easily be clipped onto a rod receiving spinal implant and reduce a fixation rod, and while clipped in place, deliver a set screw to fix the rod in a proper position to achieve the corrective spinal alignment and support for the particular surgery.

These and other objectives are achieved by the invention as described hereinafter.

SUMMARY OF THE INVENTION

A clip-on reducer tool assembly for seating a spinal fixation rod in a rod receiving implant, the tool assembly has an outer sleeve. The outer sleeve has a proximal end with a cylindrical portion having a threaded opening, a first leg extension extending therefrom to a distal end, and a second leg extension joined to the first leg extension at an intermediate location between the distal end and proximal end. The second leg extension extends from the distal end toward the proximal end to a lever end spaced from the cylindrical portion. The first and a second leg extensions at the distal end have grasping members to engage an outer surface of a rod receiving implant and a fulcrum proximally located near the intermediate location configured to enlarge the space between the leg extension at the distal end as the lever end is depressed inwardly relative to a longitudinal axis of the outer sleeve.

The clip-on reducer tool assembly further has a ring. The ring is located proximally above the fulcrum encircling portions of the first and second leg extensions to constrain and limit outward movement of the leg extensions relative to the other. The fulcrum of the outer sleeve further has a fulcrum pin fixed into the first or second leg extension abutting the opposing fulcrum projection on the other first or second leg extension. The leg extensions are spaced apart above and below the intermediate location to allow the second leg extension to pivot about the fulcrum when the lever end is depressed.

The outer sleeve further has a pair of arcuate shaped grooves. Each arcuate shaped groove is above a thin arch connecting the first and second leg extensions. The grooves are positioned adjacent distally relative to the fulcrum.

Each of the first and second leg extensions has a distal end portion for receiving and holding a slotted body of a rod receiving spinal implant. Each distal end portion is an arcuate segment having an enlarged internal chamber and an arcuate locking projection forming the grasping members configured to fit in an external groove on a slotted body of the rod receiving implant.

The clip-on reducer tool assembly further has a reducer tube and a handle. The reducer tube has a tubular shaft, a proximal end portion and a distal end portion. The tubular shaft is configured to slide into the outer sleeve. The distal end portion is rotationally coupled to the tubular shaft and has a pair of rod engaging legs convexly curved at distal ends to push against a spinal rod. The tubular shaft at the proximal end portion has an external thread to fasten the tubular shaft to the proximal end of the outer sleeve. The handle is configured to rotate the reducer tube into the outer sleeve to push the spinal rod into a seated position.

The tubular shaft has an enlarged outer bearing surface below the external thread. The enlarged bearing surface engages internal surfaces of the leg extensions of the outer sleeve locking the leg extensions to the slotted body of the rod receiving spinal implant. The rotationally coupled distal end is keyed to the outer sleeve preventing rotation at the distal end as the tubular shaft is rotated at the proximal end. The reducer tube has a longitudinally extending opening to receive a set screw and a set screw driver to secure a rod to a threaded slotted body of a spinal rod receiving implant.

A clip-on rod reducer kit can be assembled from all of the components listed above including the outer sleeve, the reducer tube, the set screw, the set screw driver, the rod receiving implant having a slotted body and a bone screw, and a spinal rod.

BRIEF DESCRIPTION OF THE DRAWINGS

The invention will be described by way of example and with reference to the accompanying drawings in which.

DETAILED DESCRIPTION OF THE INVENTION

Figure 1:
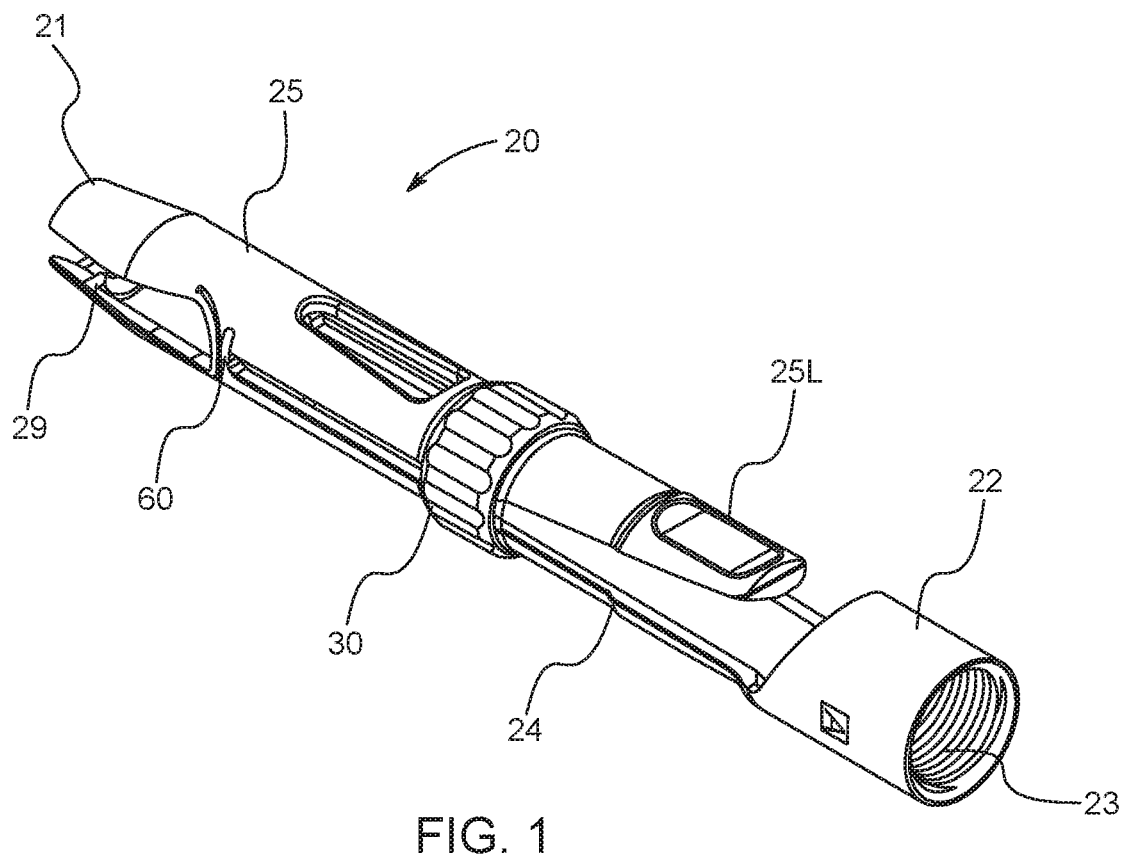
FIG. 1 is a perspective view of the outer sleeve and ring of the clip-on reducer made in accordance with the present invention.
Figure 2:
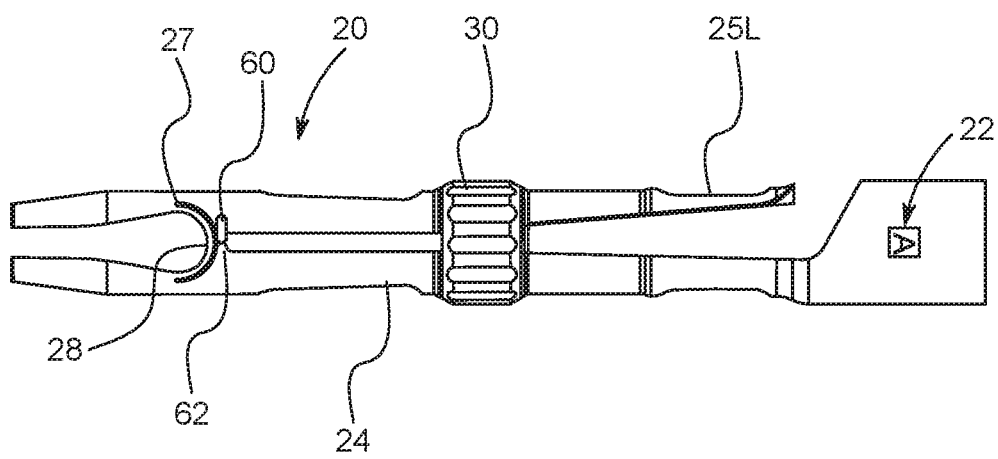
FIG. 2 is a plan side view taken from FIG. 1.
Figure 3:
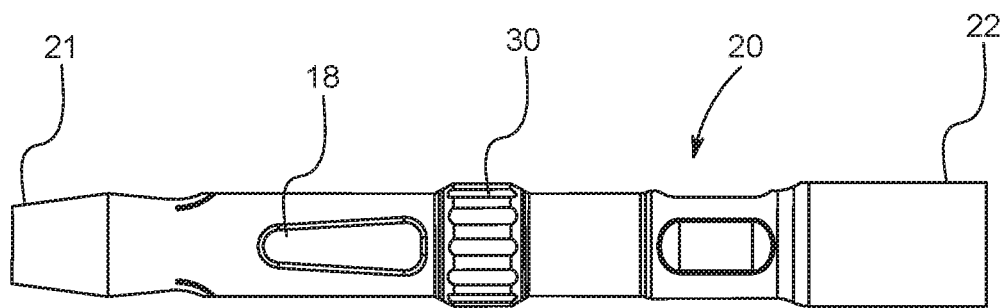
FIG. 3 is a plant top view taken from FIG. 2.

With brief reference to FIGS. 17-27, the clip-on reducer tool 10 of the present invention has two primary components, an outer sleeve 20 and a reducer tube 40. When used in a spinal surgery procedure, at a distal end 21 the outer sleeve 20 will clip on to a rod receiving spinal implant 100 and will receive the reducer tube 40 at a proximal threaded end 22 wherein the reducer tube 40 has a threaded end 43 of a tube shaft 42 that can be threaded into internal threads 23 of the outer sleeve 20 to reduce a fixation rod 12 into the slotted body 101 of the rod receiving implant 100. The FIGS. 17-27 show how the clip-on reducer tool assembly can be used in an exemplary surgical procedure which will be discussed in detail after the various components are fully explained.

Figure 4:
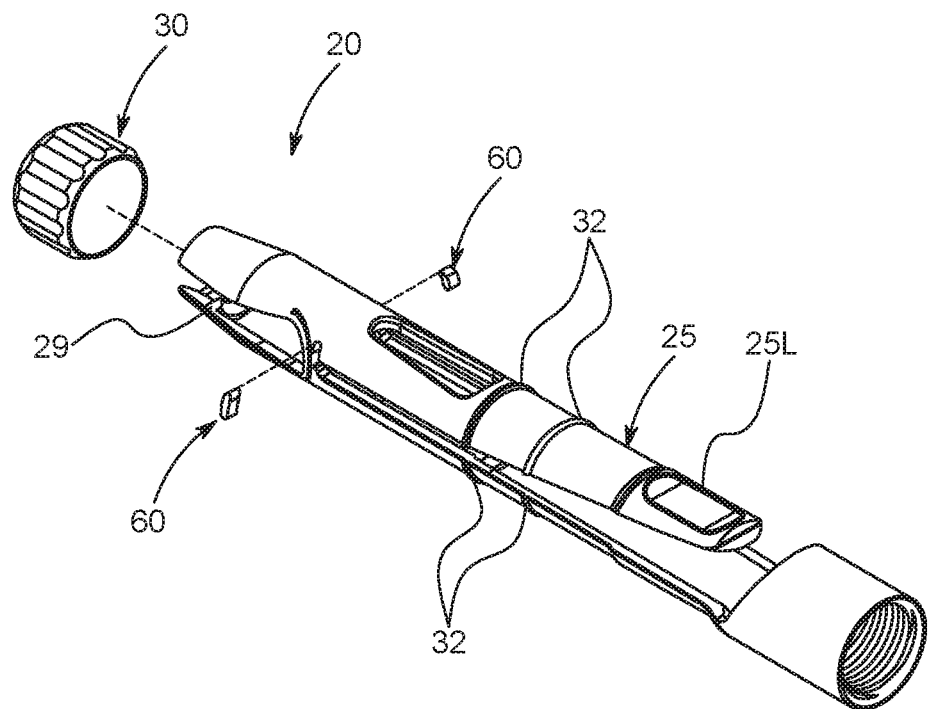
FIG. 4 is an exploded perspective view of the outer sleeve showing the ring and a pair of fulcrum pins detached from the outer sleeve.

First, with reference to FIGS. 1-10, outer sleeve 20 is shown in detail. With reference to FIGS. 1-4, the outer sleeve 20 is shown as an assembly having a ring 30 and fulcrum pins 60 shown as assembled to the outer sleeve 20 in the illustrations of FIGS. 1-3. In FIG. 4, an exploded view is shown where the ring 30 and the fulcrum pins 60 removed from the structure of the outer sleeve 20.

Figure 5:
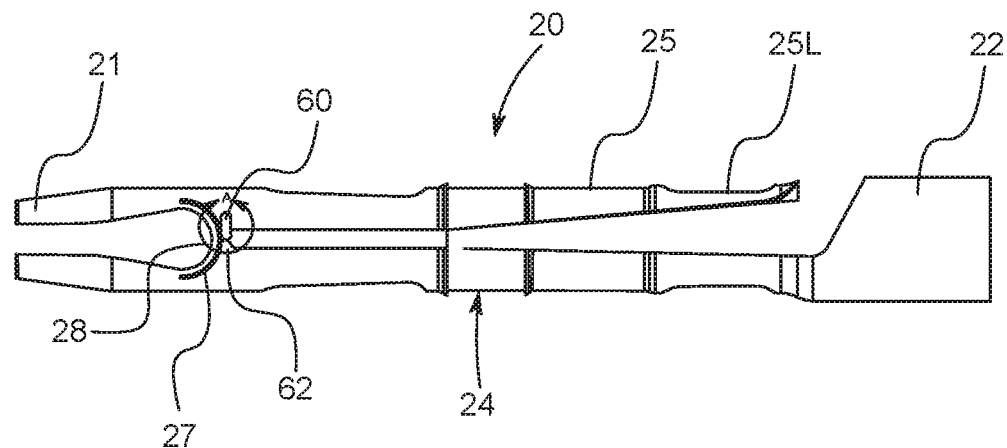
FIG. 5 is a side view of the outer sleeve showing a fulcrum pin attached.
Figure 6:
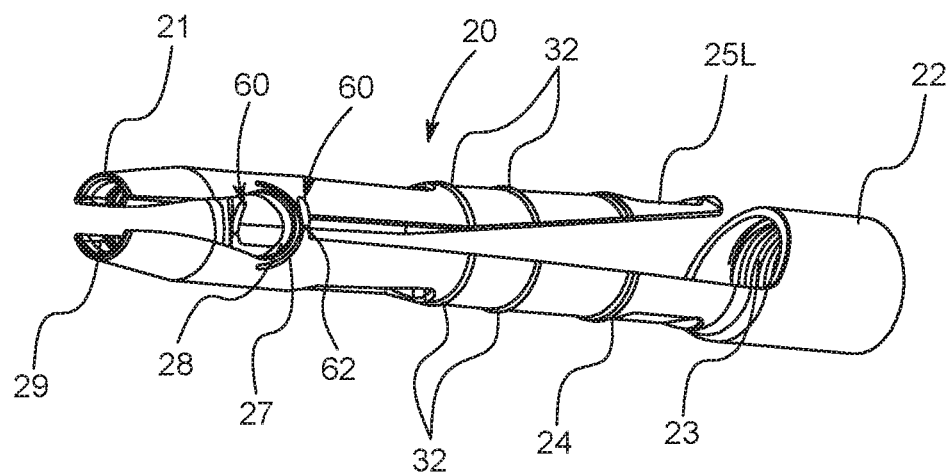
FIG. 6 is a perspective distal end view showing the fulcrum pins as fixed into the outer sleeve.

With reference to FIG. 1, the outer sleeve 20 has a proximal end 22 which is cylindrical in shape and has internal threads 23. Extending along the cylindrical portion of the proximal end 22 is a first leg extension 24 extending towards a distal end 21. The first leg extension 24 is integrally formed to the cylindrical portion and is therefore rigidly attached thereto. A second leg extension 25 is shown that extends from the distal end 21 above the first leg extension 24 towards the proximal end 22 ending at a proximal end of the leg extension 25 referred to as the lever end portion 25L. As shown, lever end portion 25L has a depression and the leg extension 24 has a complimentary depression. These depressions can be used by the surgeon so he can use his thumb to depress the lever end portion 25L of the second leg extension 25. When the second leg extension 25 is depressed, the fulcrum pin 60 pivots about a fulcrum projection 62 integral to the second leg extension 25. As the lever end 25L is depressed, the distal end 21 will pivot causing the lever end 25L to pivot about the fulcrum pin 60 thereby causing the distal end 21 to enlarge as the lever end 25L is depressed inwardly. This ability to flex the second leg extension 25 is achieved not only by the fulcrum pin 60, but directly distally below the fulcrum pin 60 on each side of the outer sleeve 20 is an arch shaped groove 27 and below the arch shaped groove 27 is a connecting portion which is a thin arch 28 that connects the second leg extension 25 to the first leg extension 24. The thin arch 28 as shown is on both sides of the outer sleeve 20. Accordingly, there is a fulcrum pin 60 on each side of the outer sleeve 20. These complimentary fulcrum pins 60 are best seen in FIG. 6 where the fulcrum pin 60 on a first side of the outer sleeve 20 is shown and a fulcrum pin 60 on an opposite side is shown. With reference to FIG. 4 and FIGS. 5 and 6, when the ring 30 is removed, it exposes projections on both the first leg extension 24 and second leg extension 25. These projections 32 are spaced such that ring 30, when pushed over, snaps in and over these projections 32. This is easily achieved because the lever end 25L can be pushed inwardly allowing the projections 32 on extension leg 25 to flex inwardly slightly which enables the ring 30 to be easily positioned between these projections 32. When this occurs, the ring 30 is securely in place. This ring 30 used to limit the amount of flexure that can occur outwardly. In other words, it creates a constraint so that the lever end 25L can only bend outwardly a limited amount constrained by the ring preventing it from moving any further out.

Figure 8:
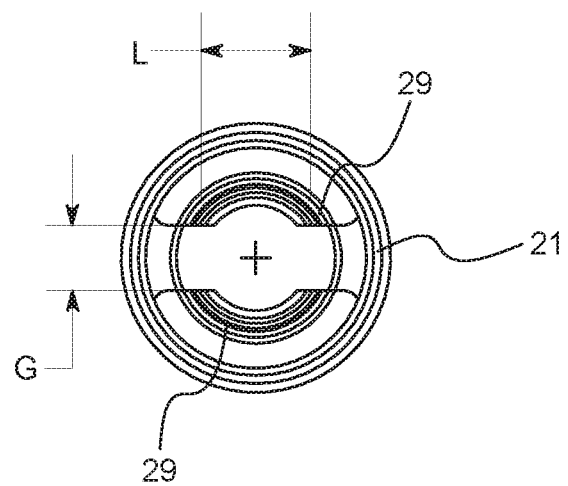
FIG. 8 is an end view of the distal end of the outer sleeve.

With reference to FIG. 8, an additional feature which is shown partially in FIGS. 1 and 4 and in FIG. 6, are projections at the distal end. The projections 29 at the distal end 21 are for grasping a slotted recess in a rod receiving spinal implant which will be discussed later. These projections 29 will extend into a groove or recess 109 in a slotted body 101 of the spinal implant 100 and will enable the outer sleeve 20 to grasp onto the spinal implant 100 and be held thereto by these projections 29. When the lever end 25L is depressed, the distal end 21 widens allowing the projections 29 to pass over the slotted body 101 of the spinal implant 100. When the lever end 25L is released the distal end 21 grips tightly into these recesses 109 of the spinal implant 100. As shown, the projections 29 span a length L and are spaced apart by a gap G, G increasing when the lever end 25L is depressed.

Figure 7:
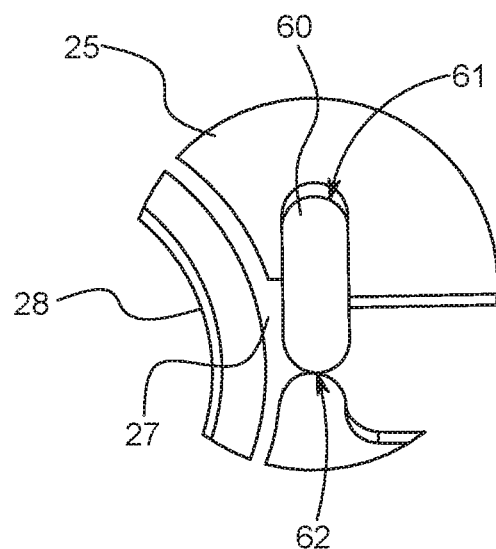
FIG. 7 is an enlarged view of the fulcrum taken along the portion 7-7 of FIG. 5.

With reference to FIG. 7, an enlarged view of the fulcrum pin 60 is shown with a fulcrum projection 62. The combination of the pair of fulcrum projections 62 on the first leg extension 24 and the pair of fulcrum pins 60 embedded in a groove 61 on the second leg extension 25 creates pivot points about which the two legs 24, 25 can flex when the lever end 25L is depressed. By having a projection 62, the amount of deflection is amplified so the distal end 21 can be opened substantially larger than would occur otherwise. To facilitate the flexure as previously discussed, the arch shaped groove 27 is shown distally below the fulcrum pin 60. There are thin arches 28 of material that spans and connects the second leg extension 25 and the first leg extension 24 on each side of the outer sleeve 20, accordingly, there are a pair of outer grooves 27 and a pair of thin arches 28 that hold the two leg extensions 24, 25 together joining them. This is the only point of connection between the first leg extension 24 and the second leg extension 25. The thin arch 28 is allowed to flex and when the lever end 25L is depressed will move slightly into or away from the groove 27 allowing flexure to occur. This flexure allows the outer sleeve 20 to open and close at the distal end 21 to grasp onto the spinal implant 100.

Figure 9:
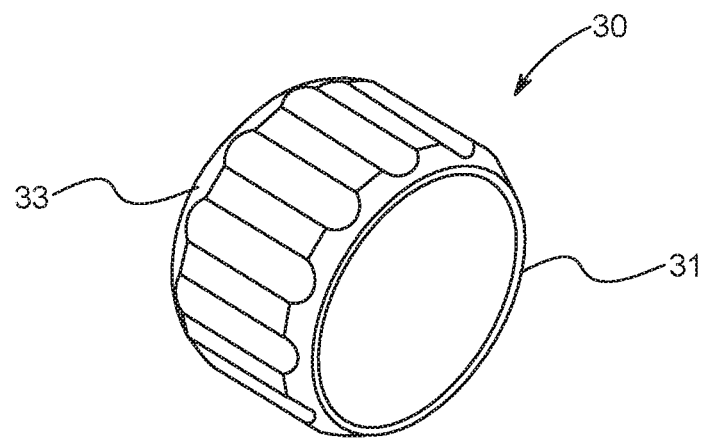
FIG. 9 is a perspective view of the ring.

With reference to FIG. 9, the ring 30 is shown having a first end 31 and a second end 33. As previously discussed, the ends 31, 33 of the ring 30 will fit between the projections 32 on the outer sleeve 20 and will be held in position to constrain the legs from splaying outwardly.

Figure 10:
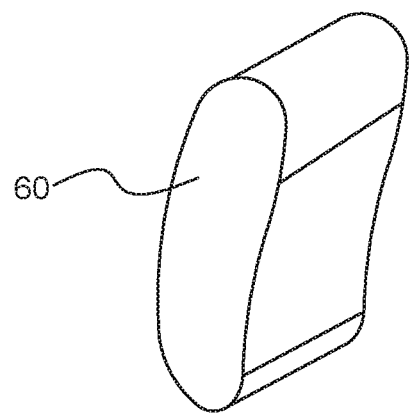
FIG. 10 is a perspective view of the fulcrum pin.
Figure 11:
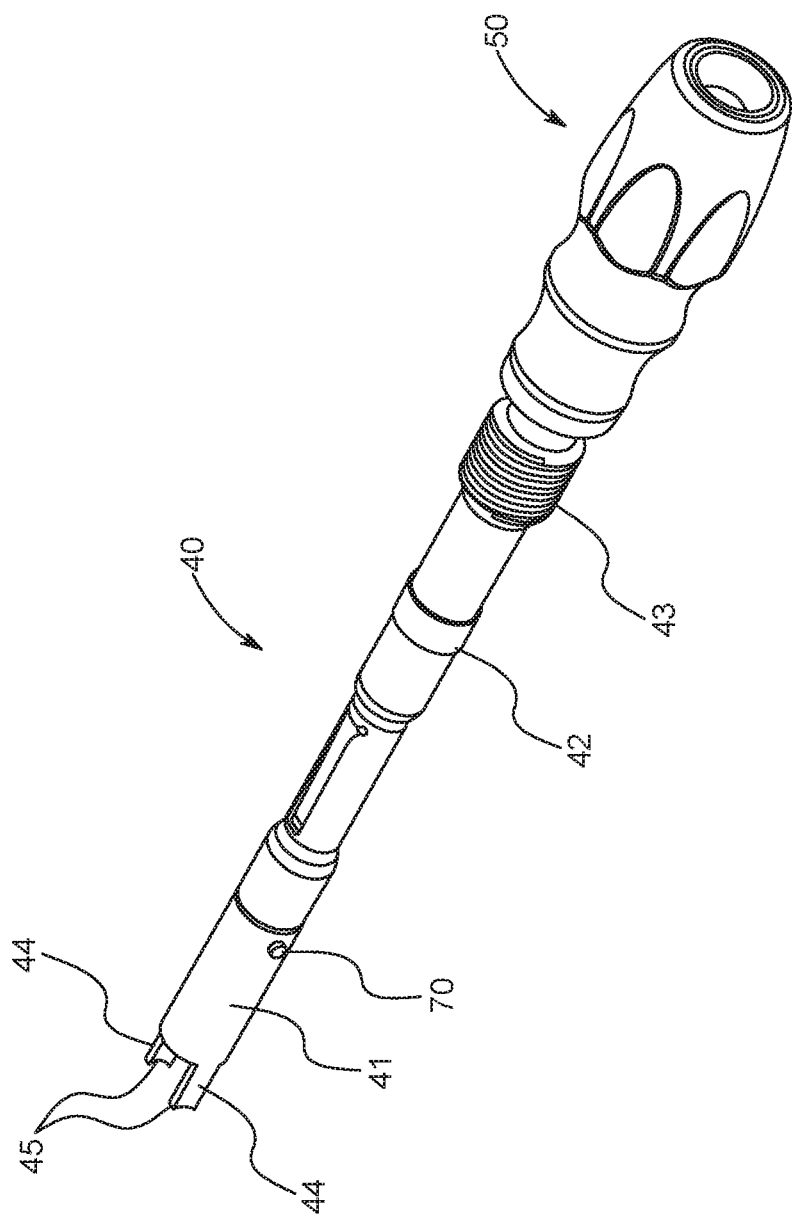
FIG. 11 is a perspective of a reducer tube of the clip-on reducer made in accordance with the present invention.

With reference to FIG. 10, an enlarged view of the fulcrum pin 60 is shown. It is slightly arcuate with curved ends and fits symmetrically on either side of the outer sleeve 20 in the cavities 61 to provide the necessary pivot fulcrum point.

Figure 12:
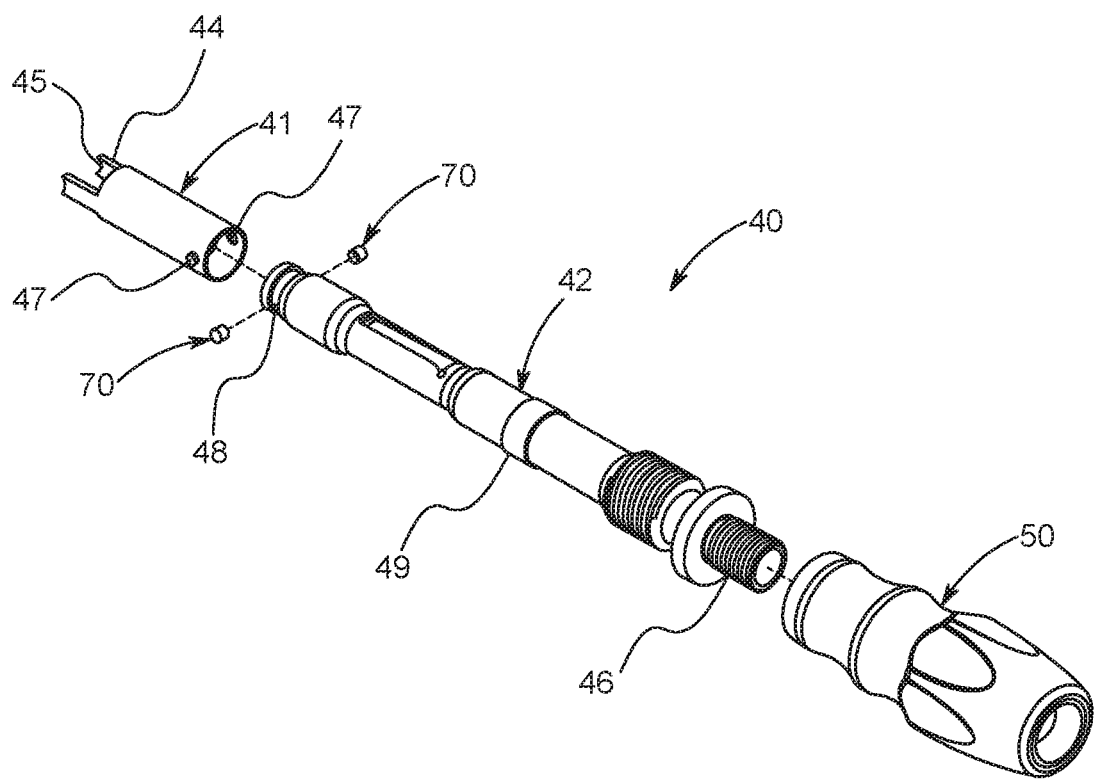
FIG. 12 is an exploded view of the reducer tube showing the rotationally coupled distal end, a pair of fixing pins and a handle removed from the tubular shaft.
Figure 13:
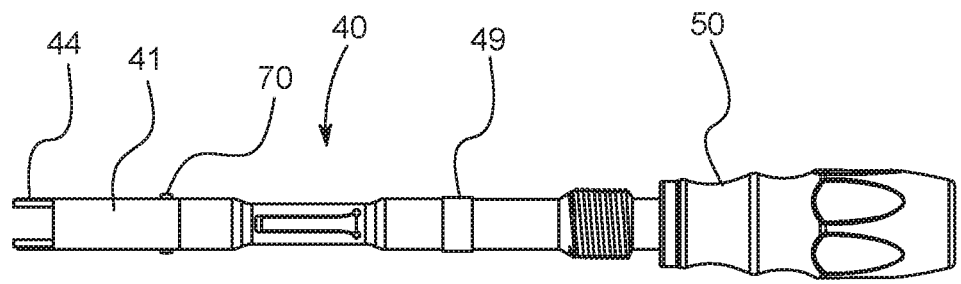
FIG. 13 is a side plan view of the reducer tube taken from FIG. 13.

With reference to FIGS. 11-16, the second primary component of the clip-on reducer 10 tool assembly is shown. The second component is the reducer tube 40. As shown in FIG. 12, the reducer tube 40 has a handle 50 rotationally fixed to the tubular shaft 42. The tubular shaft 42 has an enlarged threaded proximal end 43. The enlarged threaded proximal end 43 is adapted to thread into the internal threads 23 allowing the reducer tube 40 to fit into the proximal threaded end 22 of the outer sleeve 20 on assembly. At an opposite distal end, distal end portion 41 is illustrated, the distal end portion 41 has a pair of short leg extensions 44 with arcuate rod contacting surfaces 45 configured to push against a fixation rod when reducing the fixation rod towards a spinal implant.

With reference to FIG. 12, an exploded view of the assembly is shown. As illustrated, the handle 50 threadingly engages the tubular shaft 42. The tubular shaft 42 has a proximal threaded end 46. Once the handle 50 is assembled, it can then rotate the entire reducer tube 40. The rotationally coupled distal end portion 41 is illustrated with the short leg extensions 44 with the rod contacting surfaces 45. The rotationally coupled end portion 44 has a pair of holes 47 adapted to receive pins 70. Pins 70 when assembled into the rotationally coupled distal end portion 41 are press fit and will rotate within a groove 48 in the tubular shaft 42. On assembly, the pins 70 are not flush, however may have a slightly domed outer surface that enables the distal end portion to remain fixed pinned rotationally to the groove 48 of the tubular shaft 42 on assembly, however, still allows the tubular shaft 42 to slide freely into the outer sleeve 20 on assembly. The pins 70 will be keyed in slots formed between the two leg extensions 24, 25.

A view of the tubular shaft 42 is illustrated in FIG. 12. Showing that the tubular shaft 42 has an enlarged bearing surface portion 49 this bearing surface portion 49 is configured to limit the movement of the lever 25L when the tubular shaft 42 is fully in position in the outer sleeve 20. This happens when the tubular shaft 42 is being threaded into the outer sleeve 20. As the outer sleeve 20 is entered by the tubular shaft 42 and threadingly engaged, the bearing surface portion 49 prevents the lever end 25L from deflecting inwardly, as recalled, the ring 30 limits outward or splaying movement of the lever end 25L relative to the first leg extension 24. Accordingly, on assembly, the lever end 25L is incapable of moving once the tubular shaft 40 is moved into position. This is an important feature in that at the distal end 21, the locking of the projections into the rod receiving implant slots is fixed in that the combination of the reducer shaft 40 and the outer sleeve 20 prevents any movement at the distal end 21. Accordingly, the surgeon can feel secure that the outer sleeve 20 will not disengage from the rod receiving implant 100 and will be securely held in position as the rotational distal end 41 moves to push the fixation rod into a seated position. Interestingly, between the leg extensions 24, 25 an opening space is provided on each side of the outer sleeve 20 as the reducer shaft 40 enters the rotationally coupled distal end 41 being pinned at the groove 48 will have the outer portions of the pins 70 slide downwardly between the gap between the first and second leg extensions 24, 25. This rotationally fixes the rotationally coupled distal end 41 as the tubular shaft 42 is rotated threading into the threads 23. Accordingly, while the tubular shaft 42 is rotated, the distal end 41 can only move linearly along the axis of the reducing tool assembly 10. As this movement is further pushed inwardly, the rod positioned between the opening at the distal end 21 of the outer sleeve 20 will be pushed into the seated position.

Figure 14:
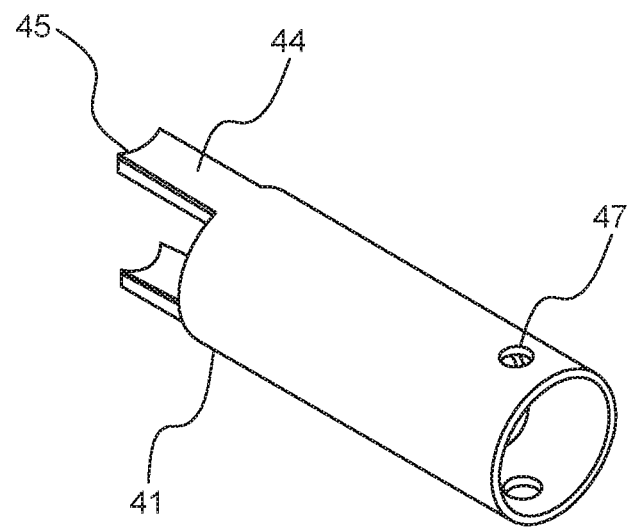
FIG. 14 is a perspective view of the rotationally coupled distal end.
Figure 15:
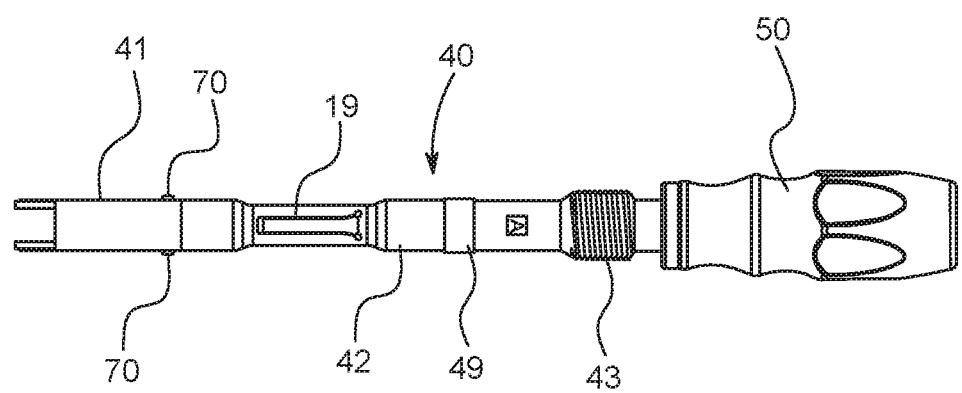
FIG. 15 is a top plan view of the reducer tube with the handle attached to the tubular shaft at the proximal end.

As shown in FIG. 14, this rotationally coupled distal end 41 is shown in a perspective and an enlarged view with the elemental features as previously discussed. FIG. 15 shows the entire assembly in a plan view wherein the domed pins 70 are shown protruding outwardly from the distal end 41 in such a fashion that they will be able to engage the slot formed between the first and second leg extensions 24, 25 as previously discussed.

Figure 16:
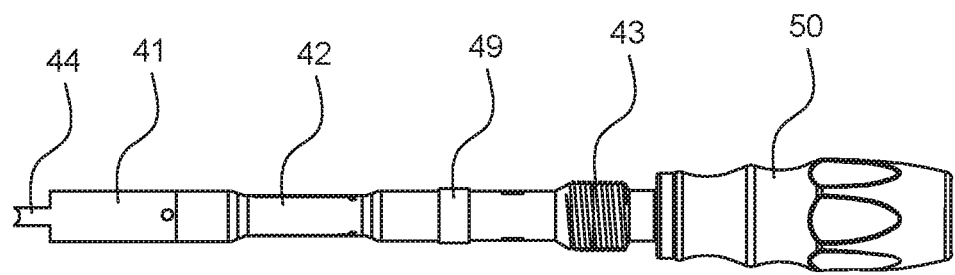
FIG. 16 is a side view of the reducer tube taken from FIG. 19.

Tubular shaft 42 clearly shows the threads 43 for engaging the proximal end of the outer sleeve 20. Additionally, a spring tang 19 is shown on each side of the tubular shaft. This spring tang 19 complimentarily fits and aligns with a window opening 18 on the outer sleeve 20. The spring tangs 19 on each side are configured to flex inwardly slightly and provide a slight detent such that when a driver with a set screw is passed through the hollow opening of the tubular shaft 42 it will meet some resistance as it passes over the spring tangs 19. FIG. 16 is a second top plan view of the assembly of the shaft 40.

With reference to FIGS. 28 through 32, a variety of components used for the fixation rod receiving spinal implant are shown.

Figure 27:
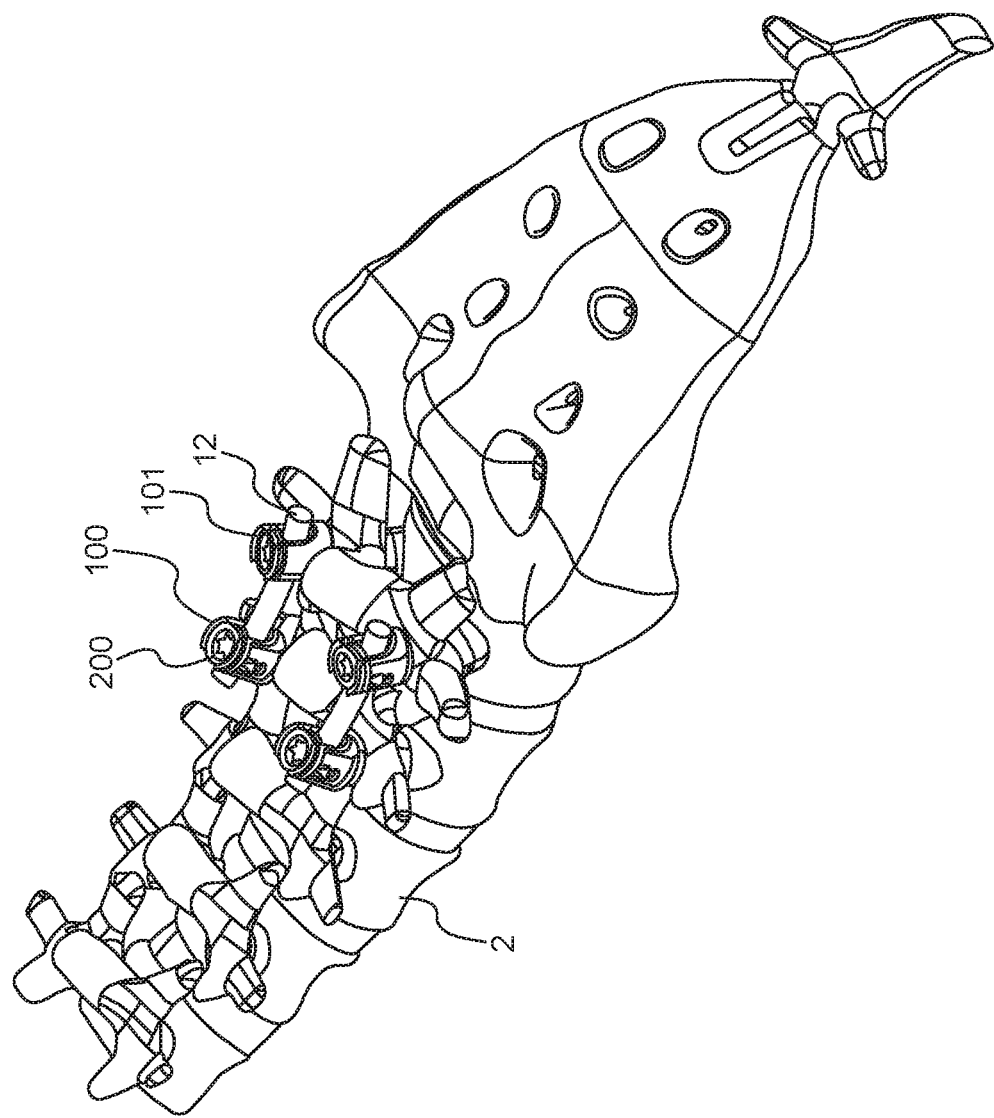
FIG. 27 shows the rod secured in the rod receiving implant at the completion of the surgical procedure.
Figure 28:
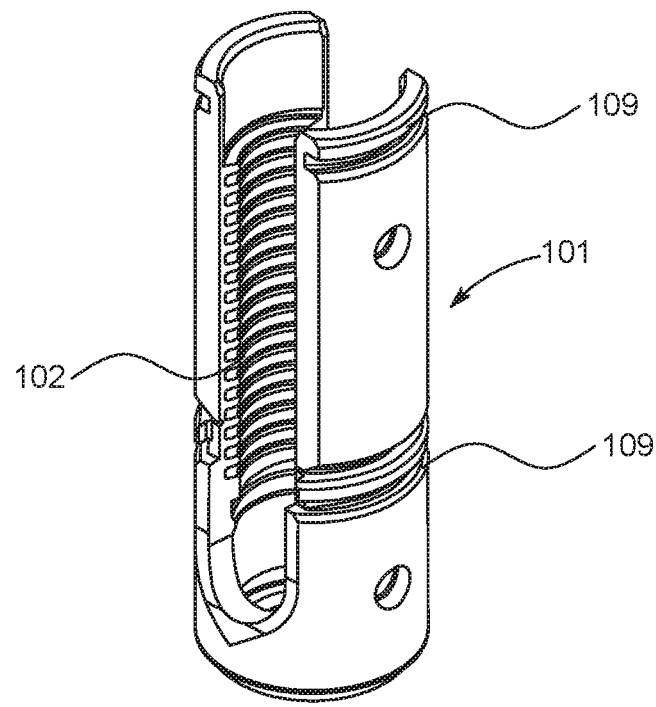
FIG. 28 is a view of an exemplary rod receiving implant.

In FIG. 28, the slotted "U" shaped body 101 of an exemplary rod receiving implant 100 is illustrated. The slotted body 101 has internal threads 102 on both sides of the slotted body and has a pair of grooves 109, the pair of grooves 109 can be grasped by the outer sleeve 20 of the clip-on reducer 10 as previously discussed. These recesses or grooves 109 are created to provide attachment and fixation positions that allow the projections 29 on the outer sleeve 20 to complimentarily fit and engage the slotted body 101 of the implant 100. As shown, this exemplary slotted body 101 has leg extensions such that they can be broken off and made shorter, typically the spinal implant 100 can be a solid piece of shorter configuration as illustrated in the embodiments shown in FIGS. 17-27.

Figure 29:
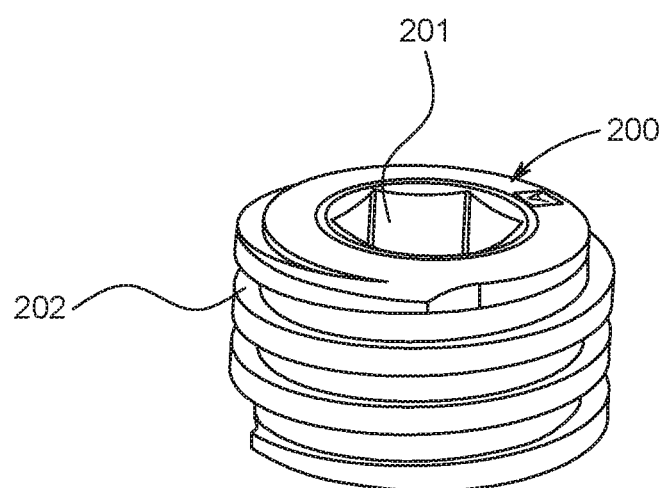
FIG. 29 is a view of an exemplary set screw.

With reference to FIG. 29, a set screw 200 is illustrated, the set screw 200 has a driver recess 201 to allow a tool to engage it to rotationally thread it along threads 202 into the slotted body 101 engaging the threads 102 thereof.

Figure 30:
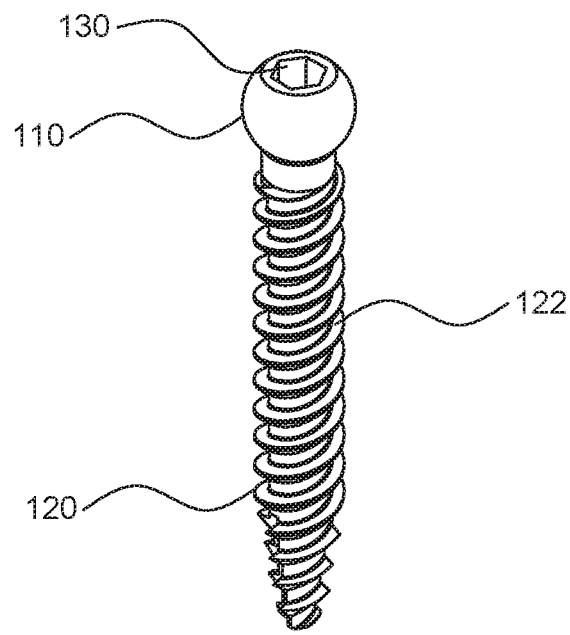
FIG. 30 is a view of an exemplary bone screw.

With reference to FIG. 30, a typical pedicle screw 120 is illustrated. The pedicle screw 120 has an enlarged head 110 and a driver receiving recess 130 to engage a tool that will allow it to be driven into the vertebral bone 2. As shown, the head 110 can have a rounded lower surface, in this configuration when positioned inside the slotted body 10 it will extend out through the bottom end and will create a polyaxial configuration such that the slotted body 101 may be moved and positioned relative to the head in a various number of angular positions. The pedicle screw 120 typically has bone engaging threads 122 as illustrated.

Figure 31:
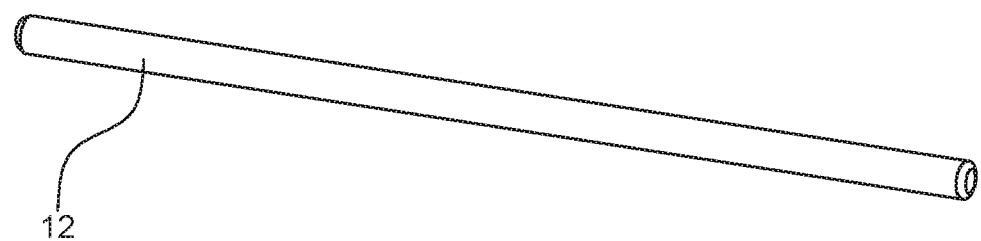
FIG. 31 is a view of an exemplary spinal rod.

With reference to FIG. 31, a typical fixation rod 12 is shown as an example. The fixation rod has a cylindrical body, generally solid, made of metals such as titanium that can be placed in the body and received in the slotted openings of the slotted body 101. As shown, the fixation rod 12 is illustrated straight, however, it can be curved and have a variety of different shapes or configurations to be used in the particular fixation procedure.

Figure 32:
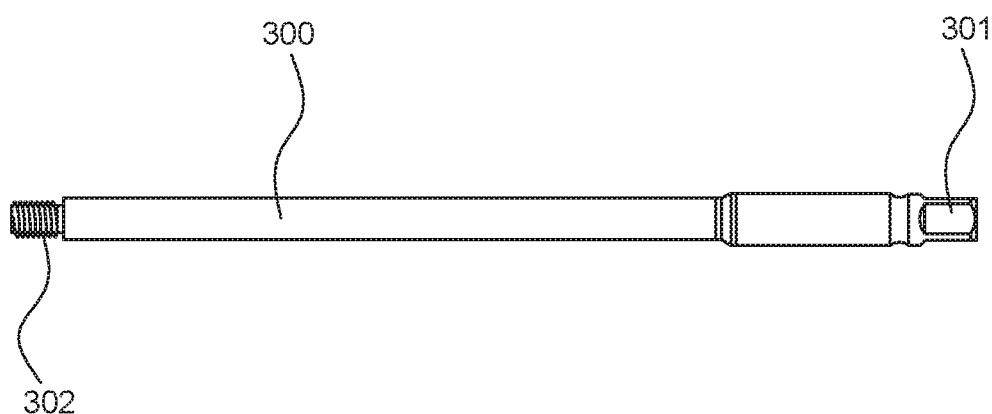
FIG. 32 is a view of an exemplary set screw driver.

With reference to FIG. 32, a set screw driver 300 is illustrated. The set screw driver 300, as shown, has a threaded end 302 to which a handle (not illustrated) can be attached. At the distal end 301 is a complimentary driver bit that is configured to fit into the recess 201 of the set screw 200 to enable it to be torqued and tightened into position.

These components can be provided as a kit or a total assembly for the surgeon, such that he can accomplish the necessary spinal fixation procedure. A clip-on rod reducer kit can be assembled from all of the components listed above including the outer sleeve, the reducer tube, the set screw, the set screw driver, the rod receiving implant having a slotted body and a bone screw, and a spinal rod.

Figure 17:
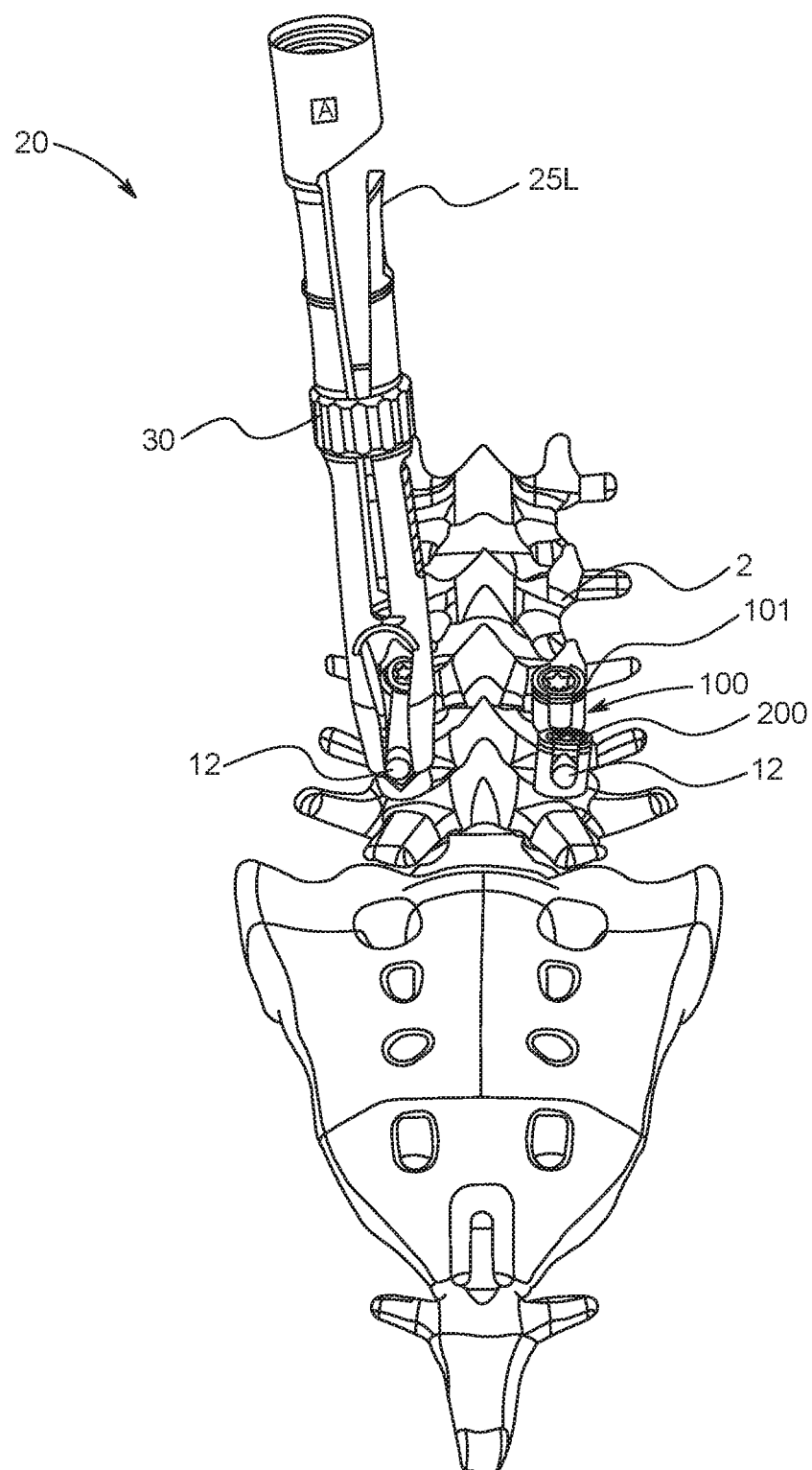
FIG. 17 is an illustration of a portion of the skeletal spine with the outer sleeve shown grasping a slotted spinal implant with a rod positioned between the legs.
Figure 18:
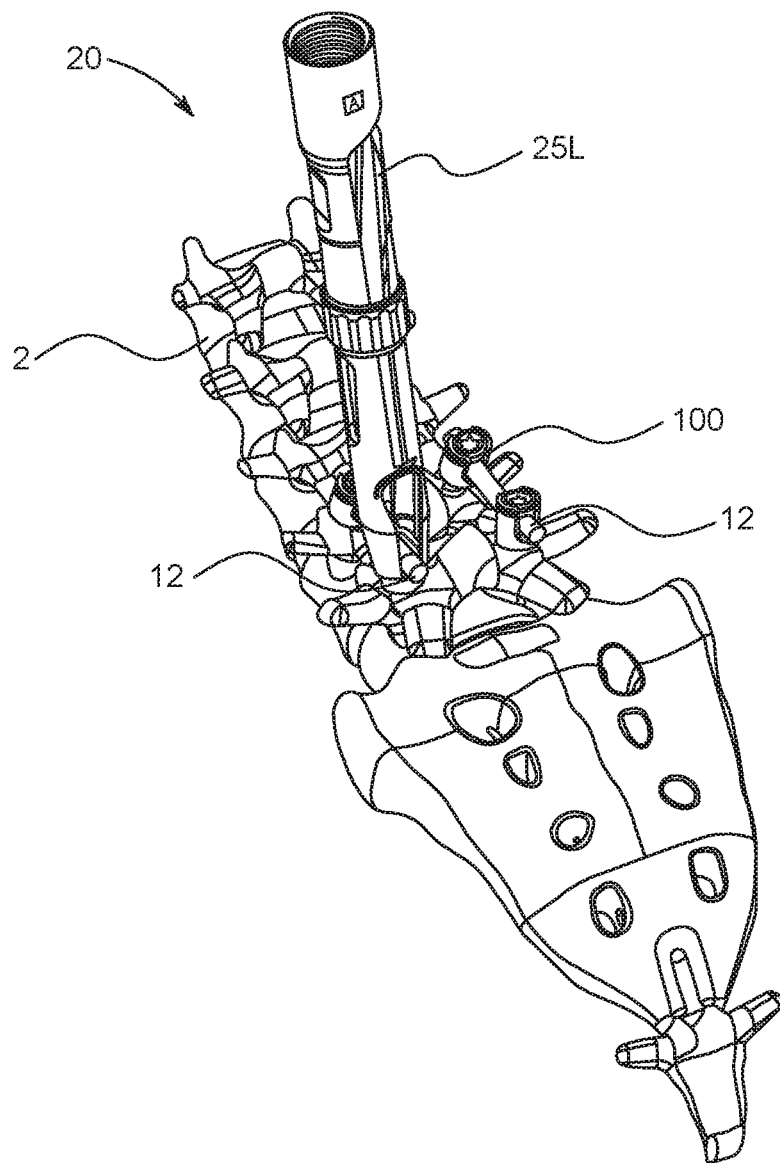
FIG. 18 is the view of FIG. 21 with the arrows showing how the outer sleeve can be manipulated to clip on the slotted body of the rod receiving spinal implant.
Figure 19:
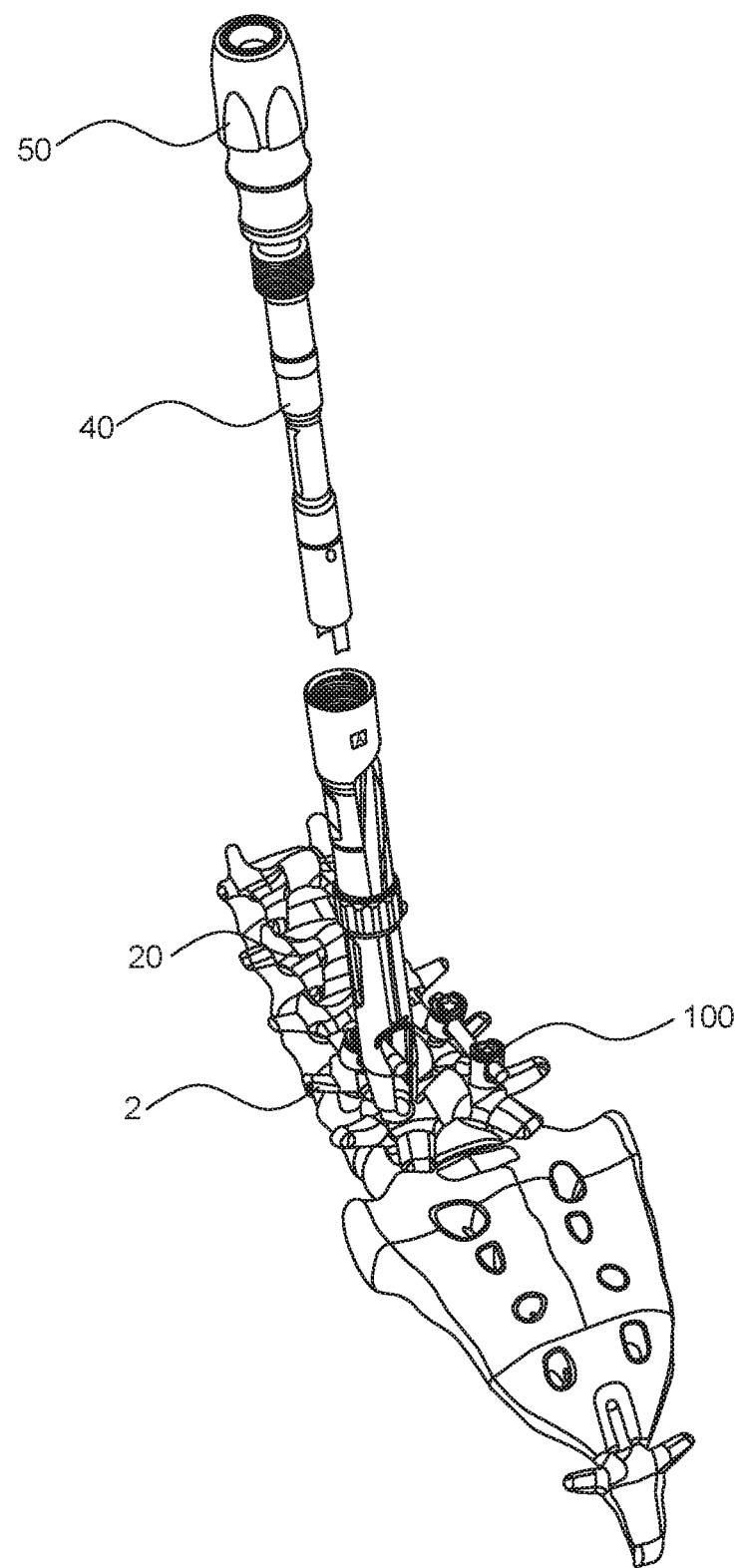
FIG. 19 shows the reducer tube positioned above the outer sleeve.
Figure 20:
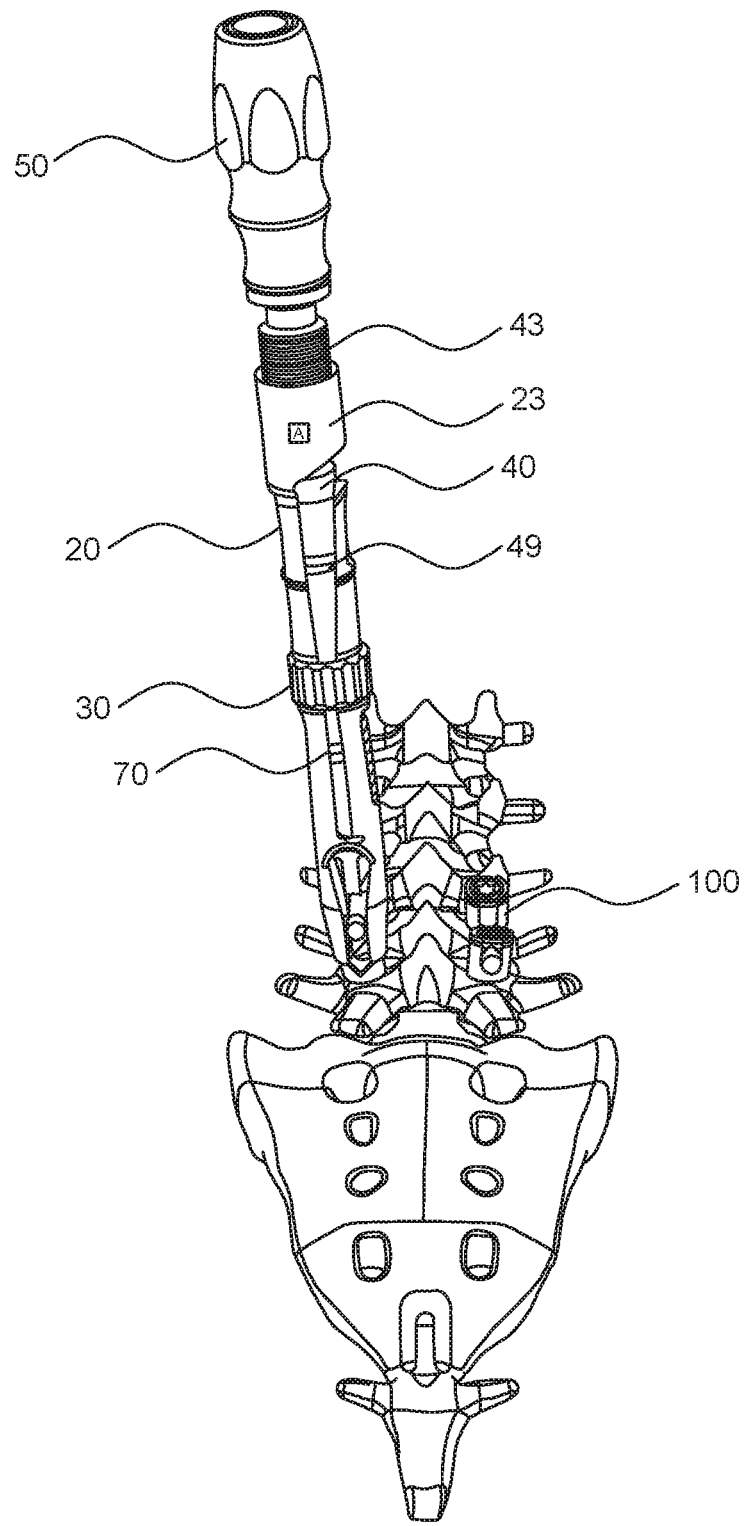
FIG. 20 shows the reducer tube engaging the outer sleeve as the reducer tube is moved distally to engage a spinal rod.
Figure 21:
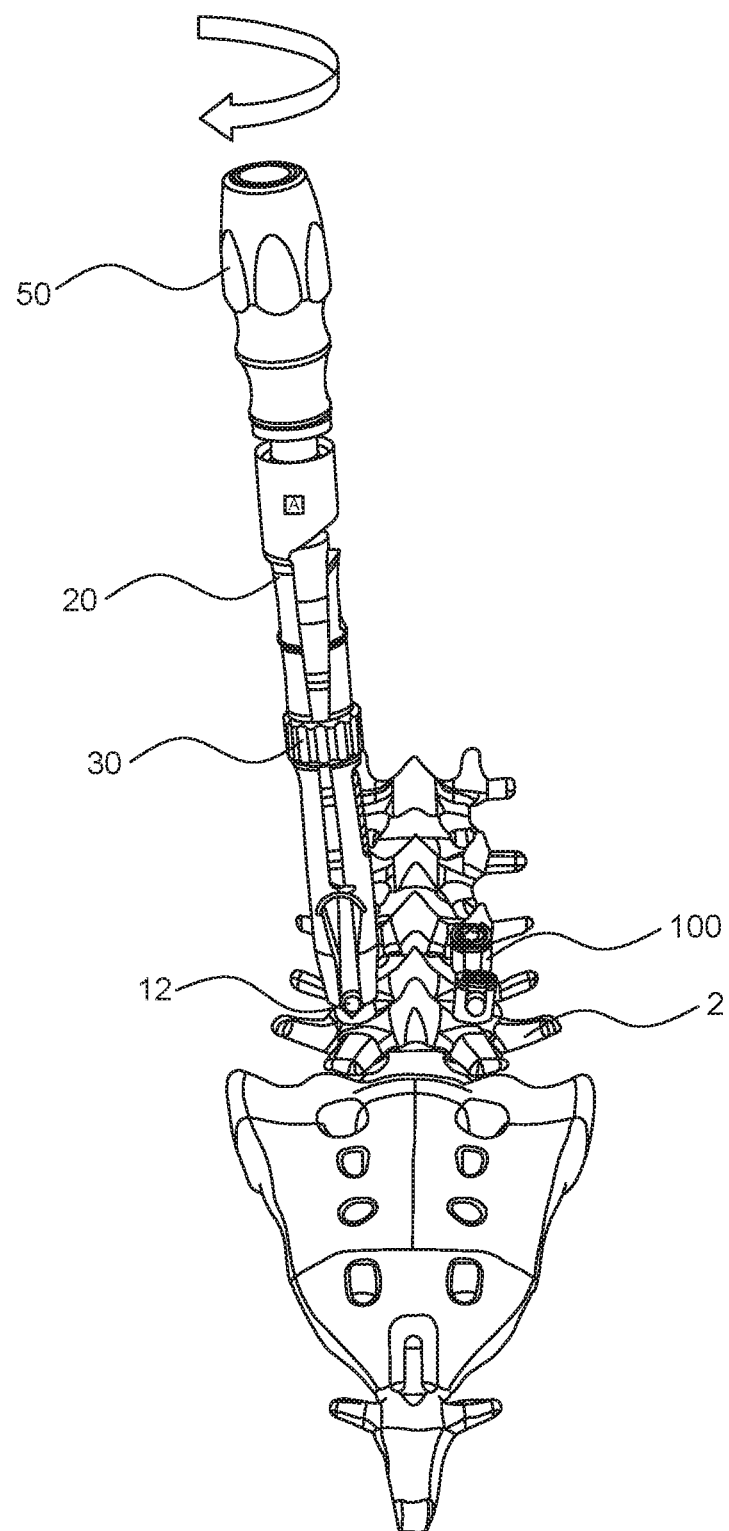
FIG. 21 shows the rotation direction to advance the reducer tube in the outer sleeve to move the spinal rod into the slotted body.
Figure 22:
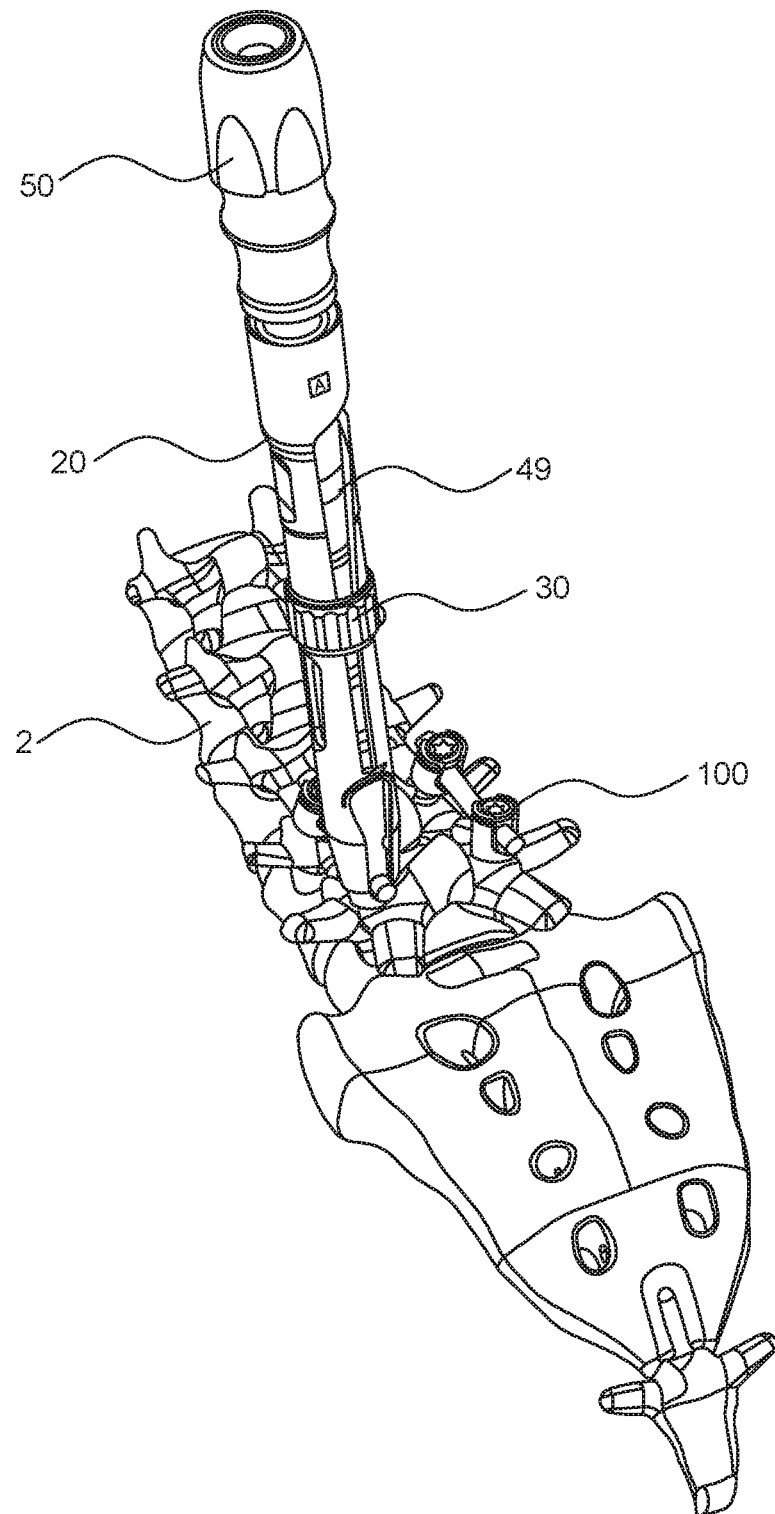
FIG. 22 shows the rod pushed in the slotted opening of the rod receiving implant and how the bearing surface of the tubular shaft locks the leg extensions.
Figure 23:
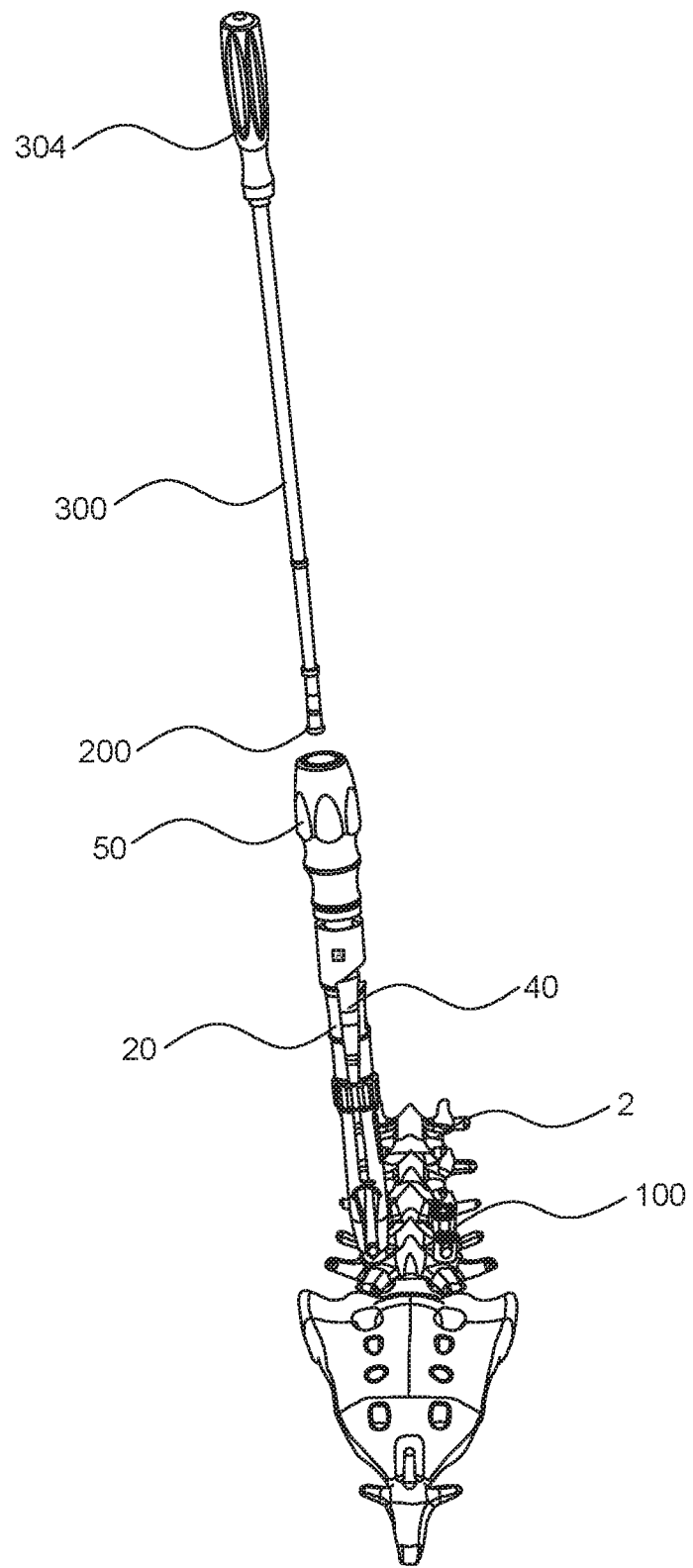
FIG. 23 shows a set screw affixed to a drive being positioned to enter the clip-on reducer assembly.
Figure 24:
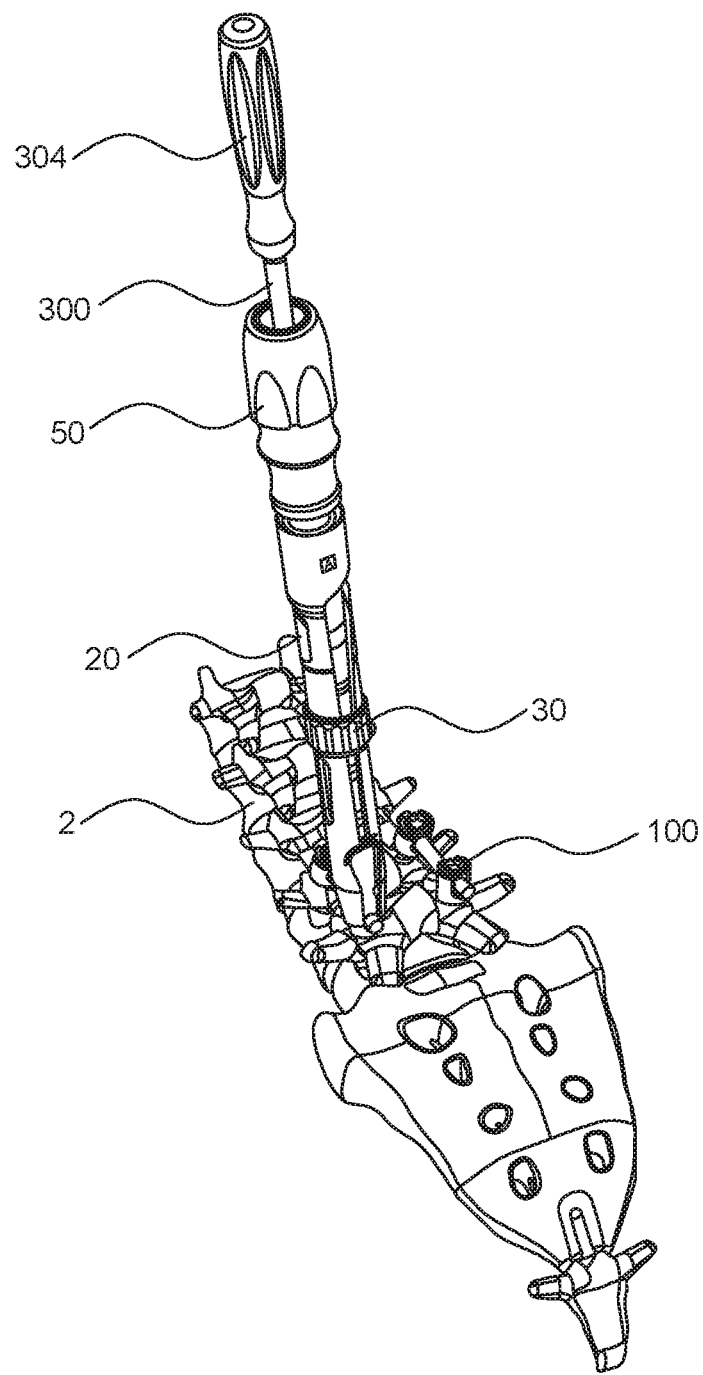
FIG. 24 shows the driver and set screw being rotated to engage the threads of the slotted body.
Figure 25:
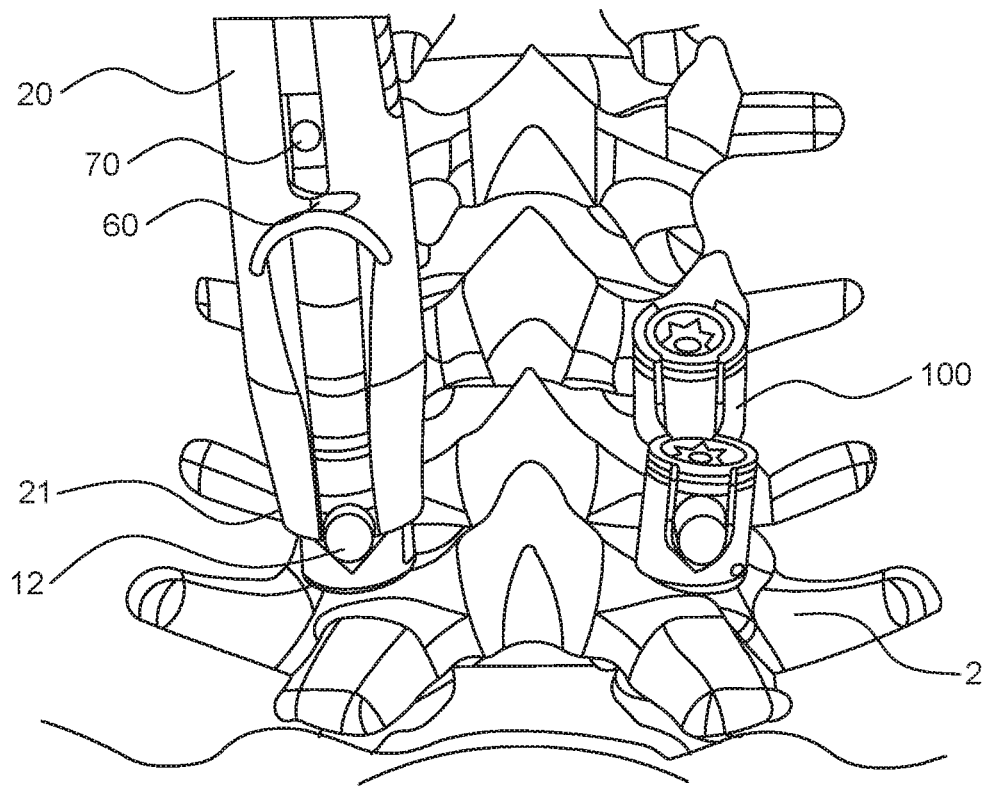
FIG. 25 shows an enlarged view of the distal end with the set screw securing the rod in the rod receiving spinal implant.
Figure 26:
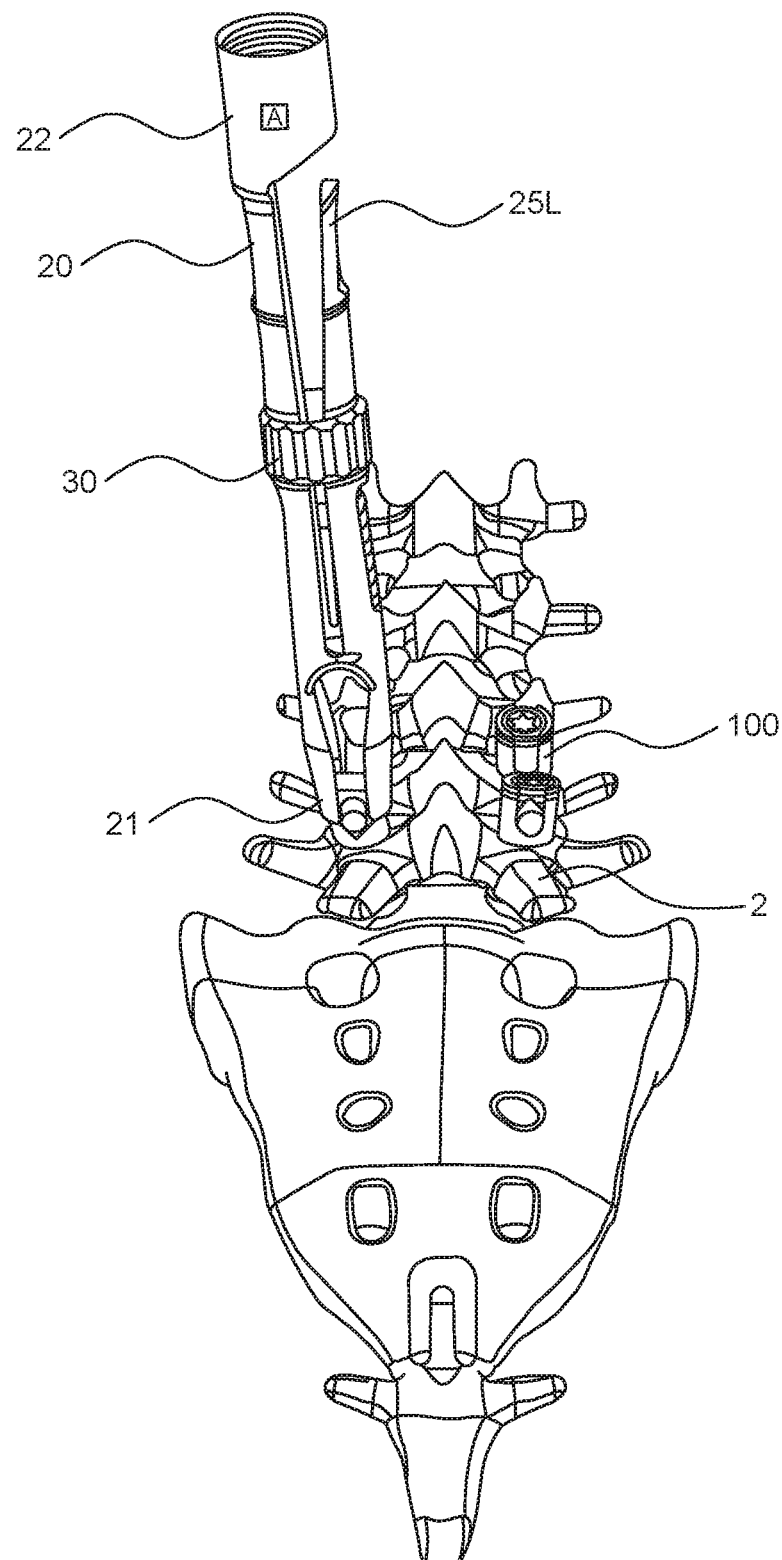
FIG. 26 shows the reducer tube removed after securing the rod and the outer sleeve being ready to disengage from the rod receiving spinal implant.

With reference to FIGS. 17-27, the clip-on reducer tool 10 is shown with an exemplary spine 2 is being used for the fixation of a rod into rod receiving spinal implants 100. As shown in FIG. 17, an initial step of using the reducer tool 10 is to provide the outer sleeve 20 to grasp onto a rod receiving spinal implant slotted body 101. As shown, on the left hand side of the figure a rod 12 is positioned between the first leg extension 24 and the second leg extension 25 with the distal end 21 grasping a recess in the slotted body 101. In this embodiment, the lever end 25L is shown in the relaxed position with the retaining ring 30 holding both leg extensions 24, 25 in a grasping position. Prior to grasping the slotted body 101, the surgeon presses the lever end 25L to enlarge the distal end 21 to engage the slotted body 101 commonly referred to as a tulip. With reference to FIG. 18, the surgeon once having grasped the slotted body 101 can then manipulate the outer sleeve 20 fore and aft to align the slotted body 101 and to adjust the alignment of the vertebrae 2 as needed. With reference to FIG. 19, the reducer tube 40 is shown above the outer sleeve 20. The reducer tube 40 as illustrated has the handle 50 connected to the reducer tube 40. In FIG. 20 the reducer tube 40 is shown being inserted into the outer sleeve 20 where the engagement threads 43 are engaging the internal threads 23 of the outer sleeve 20. In FIG. 21, rotation of the handle 50 causes the reducer tube 40 to advance as it is threadingly engaged with the outer sleeve 20. As the reducer tube 40 advances, the legs 44 at the distal end 41 engage the rod 12 with the surfaces 45. This engagement continues until the reducer tube 40 is fully inserted into the outer sleeve 20, this occurs as shown in FIG. 22. When the rod 12 is fully seated into the slotted body 101 of the rod receiving spinal implant 100. As shown in FIG. 22, in the fully engaged position, the bearing surface 49 on the tubular shaft 42 of the reducer tube 40 prevents the leg extensions 24, 25 from depressing inwardly, while the ring 30 prevents the leg extensions 24, 25 from splaying outwardly. When this occurs, the reducer tool 10 is fully locked onto the tulip or slotted body 101 and cannot be disengaged. As shown in FIG. 23, a set screw driver 300 is shown with a set screw 200 affixed to a distal end. The driver 300 is then passed through the hollow opening in the reducer tool 10 while it is fully engaged with the outer sleeve 20. As the driver is positioned internally as shown in FIG. 24 of the reducer tool 10, the handle 304 can be rotated having the set screw 200 engage internal threads 102 on the slotted body 101 of the spinal implant 100. With reference to FIG. 25, an enlarged view is shown with the reducer tool 10 having pushed the rod 12 into a fully seated position with the driver 300 shown positioning the set screw 200. This can be better seen on the right hand side with the reducer tool 10 removed where the set screw 200 is engaged and firmly securing the rod 12. This is being accomplished with the reduction tool assembly in place as shown in FIG. 25 on the left hand side. Once this is accomplished, the set screw driver 300 and the reducer tube 40 can be withdrawn from the outer sleeve 20 as shown in FIG. 26. After that occurs, the surgeon can depress the lever end 25L to disengage the outer sleeve 20 from the spinal implant 100 when this occurs, as shown in FIG. 27, the misalignment or repair to damaged vertebrae 2 can be accomplished by pairs of spinal implants 100 securing fixation rods 12, as illustrated. These figures are only exemplary of how the device 10 can be used on vertebrae of the spine, the surgeon can use the reducer tool 10 to make the necessary adjustments and alignments as needed in order to reduce a rod 12 into a spinal implant 100 as shown in the illustrated FIGS. 17-27.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:
1. A clip-on reducer comprising:
an outer sleeve comprising a first leg extension and a second leg extension, the first leg extension comprising a cylindrical portion with internal threads, the second leg extension comprising a lever end spaced from the cylindrical portion of the first leg extension, distal end portion of each of the first leg extension and the second leg extension comprising an arcuate locking projection configured to fit onto a rod receiving implant; and a reducer tube with external threads, wherein the external threads are configured to be threaded into the internal threads of the cylindrical portion of the first leg extension;

wherein the reducer tube comprises an enlarged bearing surface distal to the external threads that is configured to limit movement of the second leg extension when the reducer tube is fully in position in the outer sleeve to lock the first leg extension and the second leg extension to the rod receiving implant.

2. The clip-on reducer of claim 1, wherein the reducer tube is configured to rotate within the cylindrical portion of the first leg extension to seat a spinal fixation rod within the rod receiving implant.

3. The clip-on reducer of claim 1, wherein the reducer tube is configured to provide resistance as a set screw is passed within the reducer tube.

4. The clip-on reducer of claim 1, wherein a distal end of the reducer tube is keyed to the outer sleeve to prevent rotation of the distal end of the reducer tube as a proximal end of the reducer tube is rotated.

5. The clip-on reducer of claim 1, wherein the reducer tube comprises a tubular shaft with a spring tang on each side of the tubular shaft.

6. The clip-on reducer of claim 5, wherein the spring tang on each side of the tubular shaft is configured to provide a detent and resistance to a driver with a set screw passed within an opening of the tubular shaft.

7. The clip-on reducer of claim 1, wherein the first leg extension is joined to the second leg extension at an intermediate location located between the distal end portion and the cylindrical portion of the first leg extension and between the distal end portion and the lever end of the second leg extension.

8. The clip-on reducer of claim 7, further comprising a fulcrum proximally located near the intermediate location configured to enlarge a distance between the distal end portions of the first leg extension and second leg extension as the lever end is depressed inwardly relative to a longitudinal axis of the outer sleeve.

9. The clip-on reducer of claim 8, further comprising a ring located proximally to the fulcrum and encircling portions of the first leg extension and second leg extension to constrain and limit outward movement of the first leg extension and second leg extension relative to each other.

10. The clip-on reducer of claim 1, wherein the reducer tube further comprises a longitudinally extending shaft to deliver a set screw through the reducer tube to the rod receiving implant.

* * * * *